United States Patent
Chen et al.

(10) Patent No.: US 9,512,207 B2
(45) Date of Patent: Dec. 6, 2016

(54) ANTI-NPC2 MONOCLONAL ANTIBODIES AND A METHOD OF DETECTING FATTY LIVER TISSUE, CANCER CELLS OR CANCER TISSUE BY USING THEM

(75) Inventors: Yi-Ming Chen, Taipei (TW);
Kuan-Hsuan Chen, Taipei (TW);
Yi-Jen Liao, Taipei (TW)

(73) Assignee: NATIONAL YANG MING UNIVERSITY, Taipei (TW)

( * ) Notice: Subject to any disclaimer, the term of this patent is extended or adjusted under 35 U.S.C. 154(b) by 111 days.

(21) Appl. No.: 13/240,234

(22) Filed: Sep. 22, 2011

(65) Prior Publication Data

US 2012/0315644 A1 Dec. 13, 2012

(30) Foreign Application Priority Data

Jun. 10, 2011 (TW) .............................. 100120384 A

(51) Int. Cl.
*C07K 16/18* (2006.01)
*C07K 16/30* (2006.01)
*G01N 33/574* (2006.01)
*G01N 33/68* (2006.01)

(52) U.S. Cl.
CPC ............... *C07K 16/18* (2013.01); *C07K 16/30* (2013.01); *G01N 33/57484* (2013.01); *G01N 33/6893* (2013.01); *C07K 2317/30* (2013.01); *C07K 2317/34* (2013.01); *G01N 2800/08* (2013.01)

(58) Field of Classification Search
CPC ..... C07K 16/18; C07K 16/30; C07K 2317/30; C07K 2317/34; G01N 33/5067; G01N 33/57484; G01N 33/6893; G01N 2410/00; G01N 2800/08
USPC .... 435/7.1, 7.21, 7.23, 7.8, 7.92, 7.94, 7.95, 435/40.52, 70.21, 452, 331, 332, 344; 436/503, 514, 515, 518, 519, 536, 539, 436/548, 63, 64; 530/387.9, 388.1, 388.2, 530/388.8, 391.1, 391.3
See application file for complete search history.

(56) References Cited

U.S. PATENT DOCUMENTS

| | | | |
|---|---|---|---|
| 5,501,969 A * | 3/1996 | Hastings et al. | 435/252.33 |
| 7,842,467 B1 * | 11/2010 | Heidbrink et al. | 435/7.1 |
| 8,168,586 B1 * | 5/2012 | Fang et al. | 514/1.2 |
| 2010/0190686 A1 * | 7/2010 | Wells et al. | 514/3 |

OTHER PUBLICATIONS

Campbell, 1991. Monoclonal Antibody and Immunosensor Technology, Elsevier, Amsterdam. pp. 3-6 and 45.*
Harlow et al., 1988. Antibodies. A Laboratory Manual, Cold Spring Harbor Laboratory, Cold Spring Harbor. pp. 72-77.*
Kirchhoff et al., 1996. Molecular cloning and characterization of HE1, a major secretory protein of the human epididymis. Biology of Reproduction 54: 847-856.*
Naureckiene et al., 2000. Identification of HE1 as the second gene of Niemann-Pick C disease. Science 290: 2298-2301.*
Okamura et al., 1999. A porcine homolog of the major secretory protein of human epididymis, HE1, specifically binds cholesterol. Biochimica et Biophysica Acta 1438: 377-387.*
Ong et al., 2004. Meuronal localization and association of Niemnn Pick C2 protein (HE1/NPC2) with the postsynaptic density. Neuroscience 128: 561-570.*
Strausberg et al., 2002. Generation and initial analysis of more than 15,000 full-length human and mouse cDNA sequences. Proc. Natl. Acad. Sci. USA 99: 16899-16903, and appended listed NPC2 sequences and alignments.*
Storch et al., 2009. Niemann-Pick C2 (NPC2) and intracellular cholesterol trafficking. Biochimica et Biophysica Acta 1791: 671-678.*

* cited by examiner

*Primary Examiner* — Jacob Cheu
(74) *Attorney, Agent, or Firm* — Muncy, Geissler, Olds & Lowe P.C.

(57) ABSTRACT

The present invention is related to anti-NPC2 monoclonal antibodies, which against NPC2 or glycosylated-NPC2; and is related to a method of detecting fatty liver tissues, cancer cells or cancer tissues by evaluating the expression level of NPC2 or glycosylated-NPC2 in the cells or tissues.

10 Claims, 22 Drawing Sheets

SEQUENCE LISTING

<160> NUMBER OF SEQ ID NOS: 3

<210> SEQ ID NO 1
<211> LENGTH: 151
<212> TYPE: PRT
<213> ORGANISM: Homo sapiens

<400> SEQUENCE: 1

Met Arg Phe Leu Ala Ala Thr Phe Leu Leu Leu Ala Leu Ser Thr Ala
1               5                   10                  15

Ala Gln Ala Glu Pro Val Gln Phe Lys Asp Cys Gly Ser Val Asp Gly
            20                  25                  30

Val Ile Lys Glu Val Asn Val Ser Pro Cys Pro Thr Gln Pro Cys Gln
        35                  40                  45

Leu Ser Lys Gly Gln Ser Tyr Ser Val Asn Val Thr Phe Thr Ser Asn
    50                  55                  60

Ile Gln Ser Lys Ser Ser Lys Ala Val Val His Gly Ile Leu Met Gly
65                  70                  75                  80

Val Pro Val Pro Phe Pro Ile Pro Glu Pro Asp Gly Cys Lys Ser Gly
                85                  90                  95

Ile Asn Cys Pro Ile Gln Lys Asp Lys Thr Tyr Ser Tyr Leu Asn Lys
            100                 105                 110

Leu Pro Val Lys Ser Glu Tyr Pro Ser Ile Lys Leu Val Val Glu Trp
        115                 120                 125

Gln Leu Gln Asp Asp Lys Asn Gln Ser Leu Phe Cys Trp Glu Ile Pro
    130                 135                 140

Val Gln Ile Val Ser His Leu
145                 150

```
<210> SEQ ID NO 2
<211> LENGTH: 40
<212> TYPE: PRT
<213> ORGANISM: Homo sapiens

<400> SEQUENCE: 2

Met Arg Phe Leu Ala Ala Thr Phe Leu Leu Leu Ala Leu Ser Thr Ala
1               5                   10                  15

Ala Gln Ala Glu Pro Val Gln Phe Lys Asp Cys Gly Ser Val Asp Gly
            20                  25                  30

Val Ile Lys Glu Val Asn Val Ser
        35                  40

<210> SEQ ID NO 3
<211> LENGTH: 10
<212> TYPE: PRT
<213> ORGANISM: Homo sapiens

<400> SEQUENCE: 3

Asp Gly Val Ile Lys Glu Val Asn Val Ser
1               5                   10
```

ANTI-NPC2 MONOCLONAL ANTIBODIES AND A METHOD OF DETECTING FATTY LIVER TISSUE, CANCER CELLS OR CANCER TISSUE BY USING THEM

CROSS-REFERENCE TO RELATED APPLICATIONS

This Non-provisional application claims priority under 35 U.S.C. §119(a) on Patent Application No(s). 100120384 filed in Taiwan, Republic of China Jun. 10, 2011, the entire contents of which are hereby incorporated by reference.

FIELD OF THE INVENTION

The present invention is related to anti-NPC2 monoclonal antibodies, against NPC2 or glycosylated-NPC2; and is related to a method of detecting fatty liver tissues, cancer cells or cancer tissues by evaluating the expression level of NPC2 or glycosylated-NPC2 in the cells or tissues.

BACKGROUND OF THE INVENTION

Niemann-Pick Type C (NPC) disease is a lipid storage disorder that is characterized by progressive hepatomegaly and neurodegeneration. In this condition, lipids accumulate in the liver, kidney, spleen, bone marrow and brain. The cause of NPC is NPC1 or NPC2 gene mutation which induces the accumulation of unesterified cholesterol in the late endosomes/lysosomes.

NPC2 is a small soluble glycoprotein containing 151 amino acids, which was first characterized as a major secretory protein in human epididymis. NPC2 protein interacts with cholesterol in lysosomes to maintain the homeostasis of cholesterol in the body. In addition, in humans and mice, NPC2 is expressed in the liver and secreted into bile (Klein, Amigo et al. 2006). When NPC2 gene mutates, cholesterol will accumulate in the cell (Frolov, Zielinski et al. 2003). In addition, it has been reported that Asn-38 is never glycosylated, while Asn-58 and Asn-138 can be glycosylated. Under normal conditions, some NPC2 proteins are glycosylated only on Asn-58, and others are glycosylated both on Asn-58 and Asn-138. The Asn-58 modification is suggested to be necessary for proper NPC2 targeting to lysosomes, while the Asn-138 is non-essential. Although all glycoforms are able to bind cholesterol, one report indicated an aberrant glycosylation pattern for NPC2 in NPC1 deficient mouse livers and suggested that the cholesterol transport deficiency in NPC1 disease may arise from defects of glycosylated forms of NPC2 protein (Chikh, Vey et al. 2004).

In 1975, the method of producing "monoclonal antibody" was developed. The antibodies are mono-specific antibodies that are the same because they are made by identical immune cells that are all clones of a unique parent cell. Given almost any substance, it is possible to produce monoclonal antibodies that specifically bind to that substance; they can then serve to detect or purify that substance. Production of monoclonal antibodies involve human-mouse hybrid cells. Monoclonal antibodies are typically made by fusing myeloma cells with the spleen cells from a mouse that has been immunized with the desired antigen.

How to produce a huge amount of anti-NPC2 monoclonal antibodies and detect cancer by these antibodies is a problem to be solved.

SUMMARY OF THE INVENTION

As mentioned above, one of the purposes of the present invention is to provide an NPC2 monoclonal antibody, wherein the monoclonal antibody against N-terminal half 1-40 a.a (SEQ NO.2) of NPC protein.

Preferably, the NPC protein includes glycosylated NPC2 protein.

Preferably, the monoclonal antibody against N-terminal half 31-40 a.a (SEQ NO.3) of NPC protein.

Another aspect of the present invention is to provide a method of detecting fatty liver tissue in an organism, which includes the steps of:
 (a) Providing a tested sample form a tested organism and a normal sample;
 (b) Detecting the expression level of NPC2 protein or glycosylated NPC2 protein in the tested sample and the normal sample by the monoclonal antibody of claim 1 and evaluating the expression level, wherein the expression level of the tested sample is higher than the expression level of normal sample means the tested organism is suffered from fatty liver.

Preferably, the sample includes blood tissue, liver tissue or the combination thereof.

Preferably, the sample is liver cell.

Another aspect of the present invention is to provide a method of detecting cancer in an organism, which includes the steps of:
 (a) Providing a tested sample form a tested organism and a normal sample;
 (b) Detecting the expression level of NPC2 protein or glycosylated NPC2 protein in the tested sample and the normal sample by the monoclonal antibody of claim 1 and evaluating the expression level, wherein the expression level of the tested sample is higher than the expression level of normal sample means the tested organism is suffered from cancer.

Preferably, the cancer includes breast cancer, colon cancer, lung cancer and prostate cancer.

Another aspect of the present invention is to provide a method of detecting cancer in an organism, which includes the steps of:
 (a) Providing a tested sample form a tested organism and a normal sample;
 (b) Detecting the expression level of NPC2 protein or glycosylated NPC2 protein in the tested sample and the normal sample by the monoclonal antibody of claim 1 and evaluating the expression level, wherein the expression level of the tested sample is lower than the expression level of normal sample means the tested organism is suffered from cancer.

Preferably, the cancer includes hepatic cancer or kidney cancer.

Preferably, the detecting method includes western-blotting, immunoprecipitation and immunohistochemistry.

Preferably, the sequence of NPC2 is:

```
                                         (SEQ NO. 1)
MRFLAATFLLLALSTAAQAEPVQFKDCGSVDGVIKEVNVSPCPTQPCQL

SKGQSYSVNVTFTSNIQSKSSKAVVHGILMGVPVPFPIPEPDGCKSGIN

CPIQKDKTYSYLNKLPVKSEYPSIKLVVEWQLQDDKNQSLFCWEIPVQI

VSHL.
```

DETAILED DESCRIPTION OF THE INVENTION

Figure 1A:
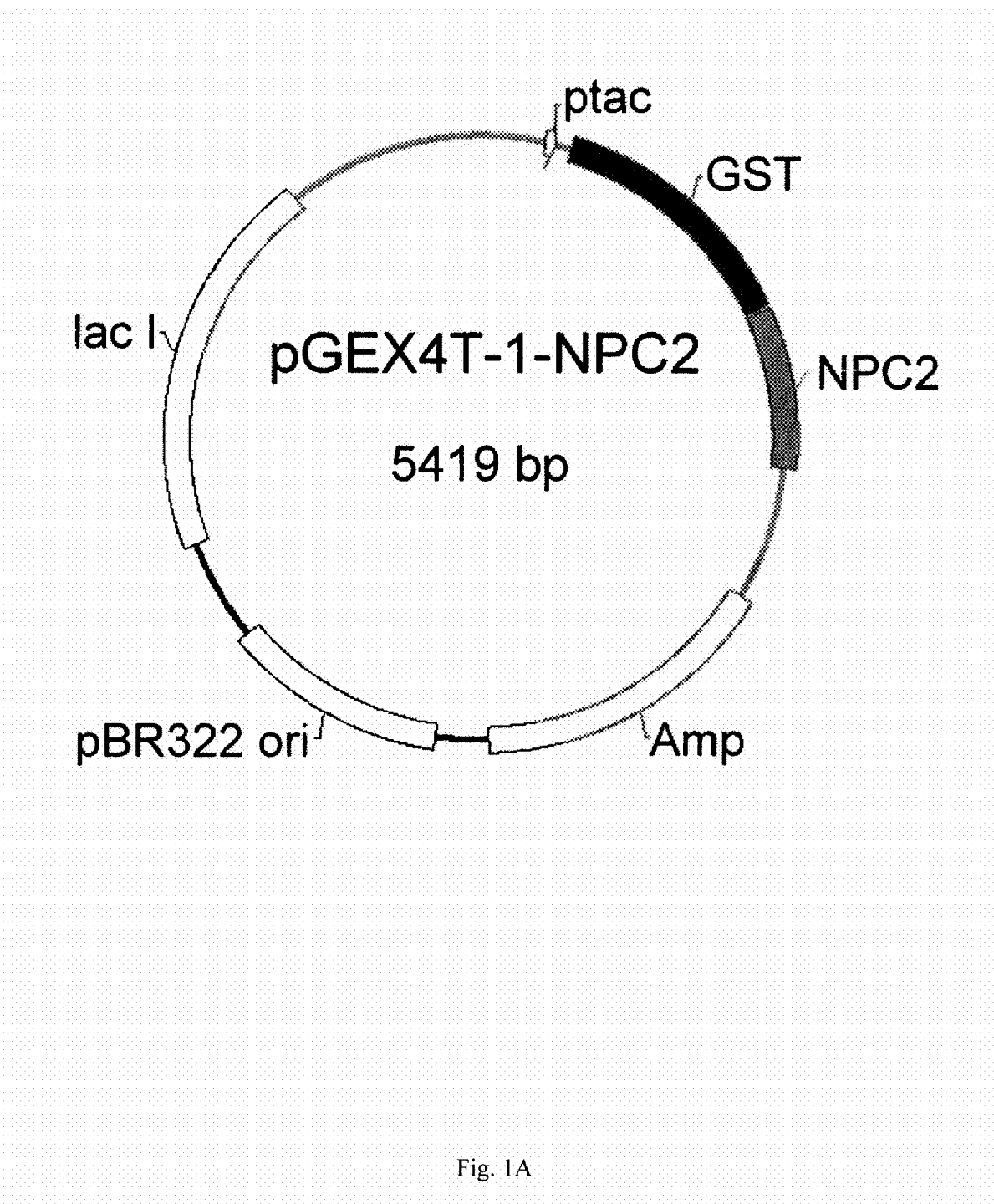
FIG. 1A illustrates GEX4T-1-NPC2 plasmid of expressing GST-NPC2 protein.

The anti-NPC2 monoclonal antibody of the present invention can be identified by western blotting, immunoprecipitation and immunohistochemistry. The epitope region of present invention has a high sensitivity to NPC2 or glycosylated-NPC2. Wherein the sequence of NPC2 is:

(SEQ NO. 1)
MRFLAATFLLLALSTAAQAEPVQFKDCGSVDGVIKEVNVSPCPTQPCQL

SKGQSYSVNVTFTSNIQSKSSKAVVHGILMGVPVPFPIPEPDGCKSGIN

CPIQKDKTYSYLNKLPVKSEYPSIKLVVEWQLQDDKNQSLFCWEIPVQI

VSHL.

One of aspect of the present invention is to provide a method of detecting fatty liver tissue in an organism, which includes the steps of:
  (a) Providing a tested sample form a tested organism and a normal sample;
  (b) Detecting the expression level of NPC2 protein or glycosylated NPC2 protein in the tested sample and the normal sample by the monoclonal antibody of claim 1 and evaluating the expression level, wherein the expression level of the tested sample is higher than the expression level of normal sample means the tested organism is suffered from fatty liver.

Wherein the sample can be, but not limited to blood tissue, liver tissue or the combination thereof.

Wherein the sample can be, but not limited to liver cell.

Another aspect of the present invention is to provide a method of detecting cancer in an organism, which includes the steps of:
  (a) Providing a tested sample form a tested organism and a normal sample;
  (b) Detecting the expression level of NPC2 protein or glycosylated NPC2 protein in the tested sample and the normal sample by the monoclonal antibody of claim 1 and evaluating the expression level, wherein the expression level of the tested sample is higher than the expression level of normal sample means the tested organism is suffered from cancer.

Wherein the cancer can be, but not limited to breast cancer, colon cancer, lung cancer and prostate cancer.

Another aspect of the present invention is to provide a method of detecting cancer in an organism, which includes the steps of:
  (a) Providing a tested sample form a tested organism and a normal sample;
  (b) Detecting the expression level of NPC2 protein or glycosylated NPC2 protein in the tested sample and the normal sample by the monoclonal antibody of claim 1 and evaluating the expression level, wherein the expression level of the tested sample is lower than the expression level of normal sample means the tested organism is suffered from cancer.

Wherein the cancer can be, but not limited to hepatic cancer and kidney cancer.

Wherein the detecting method can be, but not limited to western-blotting, immunoprecipitation and immunohistochemistry.

Wherein the sequence of NPC2 is: MRFLAATFLLLAL-STAAQAEPVQFKDCGSVDGVIKEVNVSPCPTQPCQL-SKGQSYSVNV TFTSNIQSKSSKAVVHGILMGVPVP-FPIPEPDGCKSGINCPIQKDKTYSYLNKLPVKSEYPS IKLVVEWQLQDDKNQSLFCWEIPVQIVSHL (SEQ NO.1).

As mentioned above, the monoclonal antibodies of the present invention specific recognize NPC2 and glycosylated-NPC2. Besides, the present invention provides a method of detecting cancer by the monoclonal antibodies.

EXAMPLES

Example 1

Generate NPC2 Monoclonal Antibodies

Figure 1B:
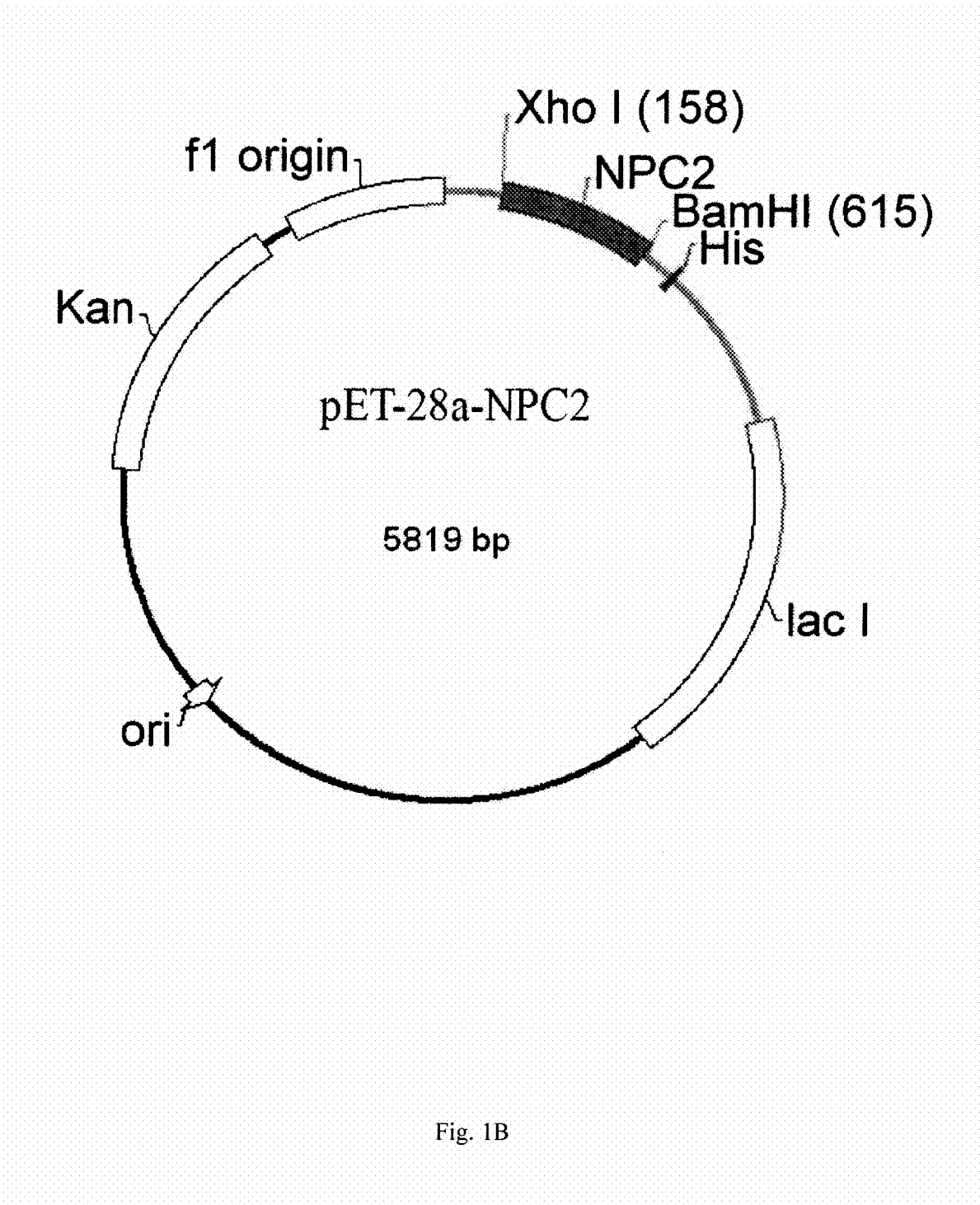
FIG. 1B illustrates pET28a-NPC2 plasmid of expressing His-NPC2 protein.

To generate a series of monoclonal antibodies against NPC2, purified GST-NPC2 or His-NPC2 were mixed with Freund's complete (for the initial immunization) or incomplete (for the booster injections) adjuvant (Sigma Co., St. Louis, Mo., USA) and the resultant mixture was used as an immunogen. His-NPC2 RP was used as a screened antigen for antibody arising from GST-NPC2 RP, and vice versa (FIG. 1). Mouse mAbs were produced by a hybridoma technique. The hybridomas were dispensed into six 96-well plates and cultured in a HAT medium. The culture supernatants were screened using enzyme immunoassay (EIA) with GST-NPC2 RP and His-NPC2 RP. Hybridoma cells with high optic density were confirmed with Western blot assay immediately. Each well of cells with positive results was subcloned into a 96-well plate with a cell density of 0.5 cell per well. The resultant single clone with positive results was inoculated at a dosage of $5 \times 10^6$ to a BALB/c mouse, which has been primed with 0.5 ml pristine (Sigma-Aldrich) previously. Monoclonal antibodies were purified from the mouse ascites with protein-A antibody purification kits (Pro-Chem Inc. Acton, Mass.) and concentrated using Centricon Plus-80 columns (Millipore). The isotype of each mAb was determined using a commercial kit (SouthernBiotech, Birmingham, Ala.). High-tittered mAbs purified from ascites were diluted with 0.1M $NaHCO_3$ (pH=8.6) to a concentration of 100 μg/ml, and added to 6 ml sterile polystyrene Petri dishes. After coating overnight at 4° C. in a humidified container, the plates were blocked with the blocking buffer (0.1 M NaHCO$_3$ pH=8.6, 5 mg/ml BSA, 0.02% NaN3, with a sterilized filter, stored at 4° C.) and incubated for at least 1 hour at 4° C. M13 phages displaying random heptapeptides at the N-terminus of its minor coat protein (pIII) were subsequently added (Ph.D.-7™ Phage Display Peptide Library, New England Biolabs Inc.). The phages bound to the plates were selected and repeatedly screened for 3 times before they were subjected to DNA sequencing.

Anti-NPC2 monoclonal antibodies (including 14-8D. 5-5B, 5-4B, 4-12C, 3-6B, 2-7D, 1-5B and 1-2G) had been generated and characterized in table 1.

TABLE 1

Anti-NPC2 monoclonal antibodies: 14-8D. 5-5B, 5-4B, 4-12C, 3-6B, 2-7D, 1-5B and 1-2G

| monoclonal antibodies | gene name | Immunoglobulin Heavy chain | Light chain | epitope |
|---|---|---|---|---|
| 1-2G | NPC2 | IgG2a | kappic | N-terminal 1~40 amino acid |
| 1-5B | NPC2 | IgG2a | kappic | N-terminal 1~40 amino acid |
| 2-7B | NPC2 | IgG2a | kappic | N-terminal 1~40 amino acid |
| 3-6B | NPC2 | IgG2a | kappic | N-terminal 1~40 amino acid |
| 4-12C | NPC2 | IgG2a | kappic | N-terminal 1~40 amino acid |
| 5-4B | NPC2 | IgG2a | kappic | N-terminal 1~40 amino acid |
| 5-5B | NPC2 | IgG2a | kappic | N-terminal 1~40 amino acid |
| 14-8D | NPC2 | IgG2a | kappic | N-terminal 1~40 amino acid |

Example 2

Confirm the Reactivity of NPC2 Monoclonal Antibodies

Figure 2:
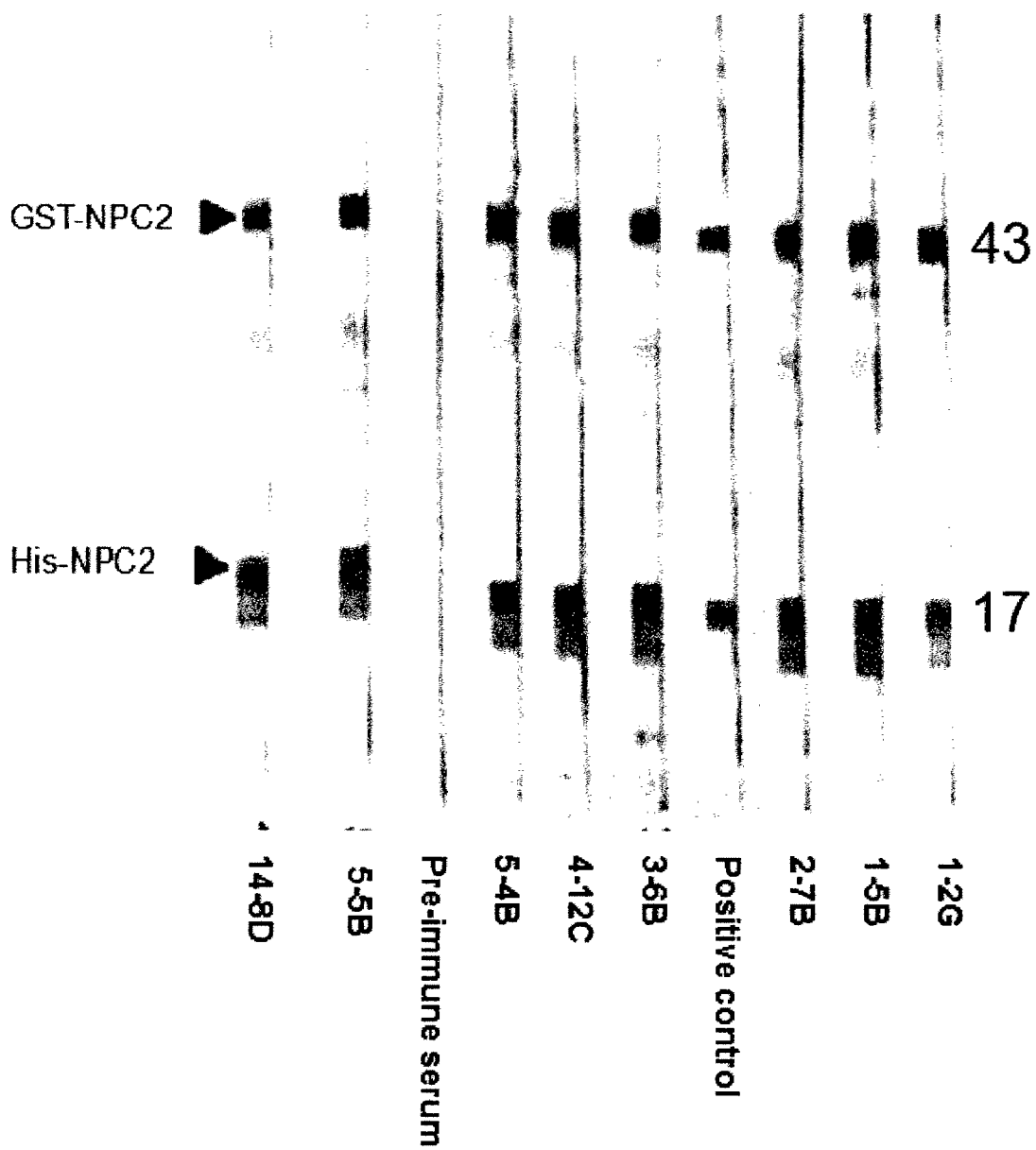
FIG. 2 shows western-blotting analysis of different kinds of monoclonal antibodies against His-NPC2 and GST-NPC2.
Figure 3:
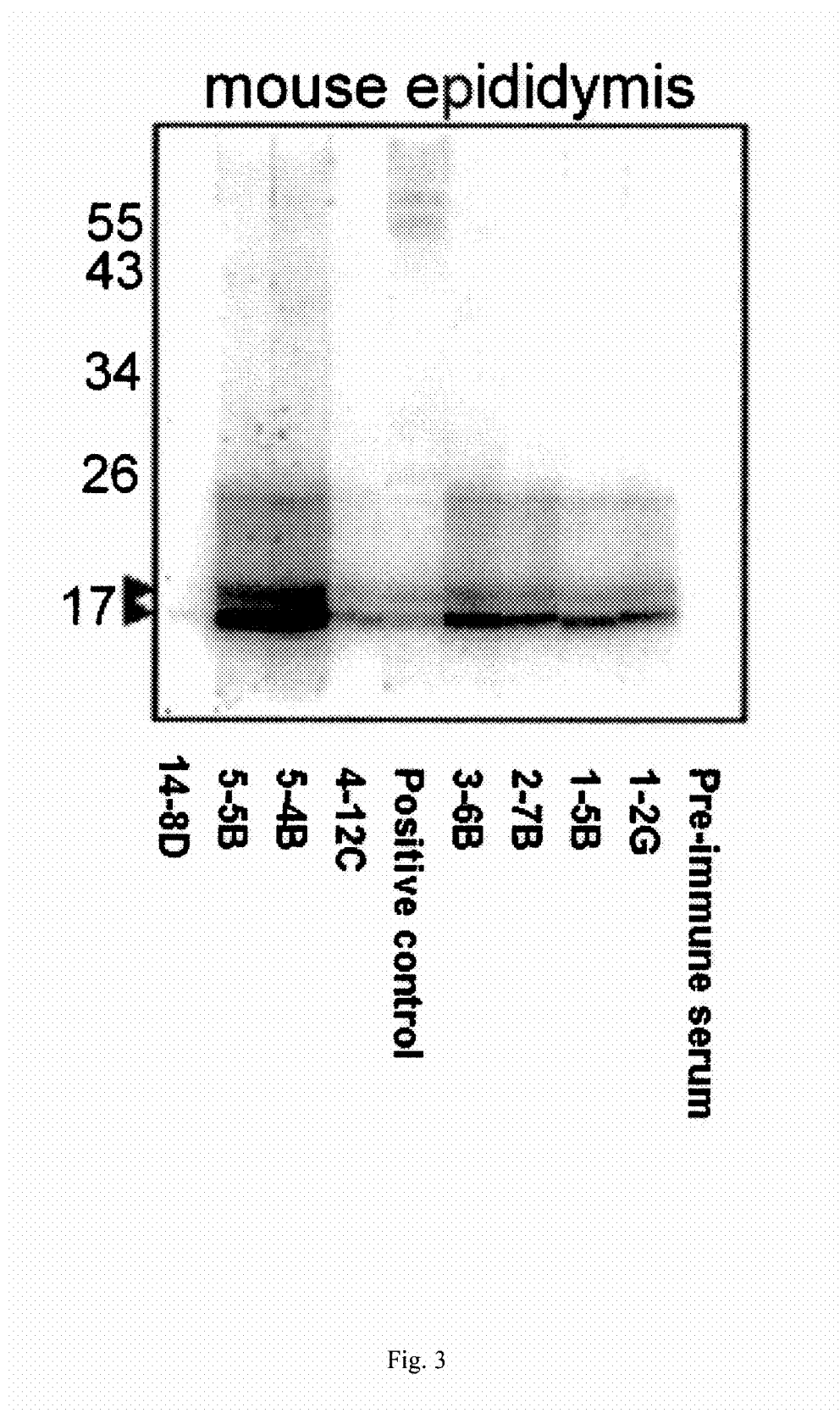
FIG. 3 shows western-blotting analysis of different kinds of monoclonal antibodies against NPC2 in mouse epididyme.
Figure 4A:
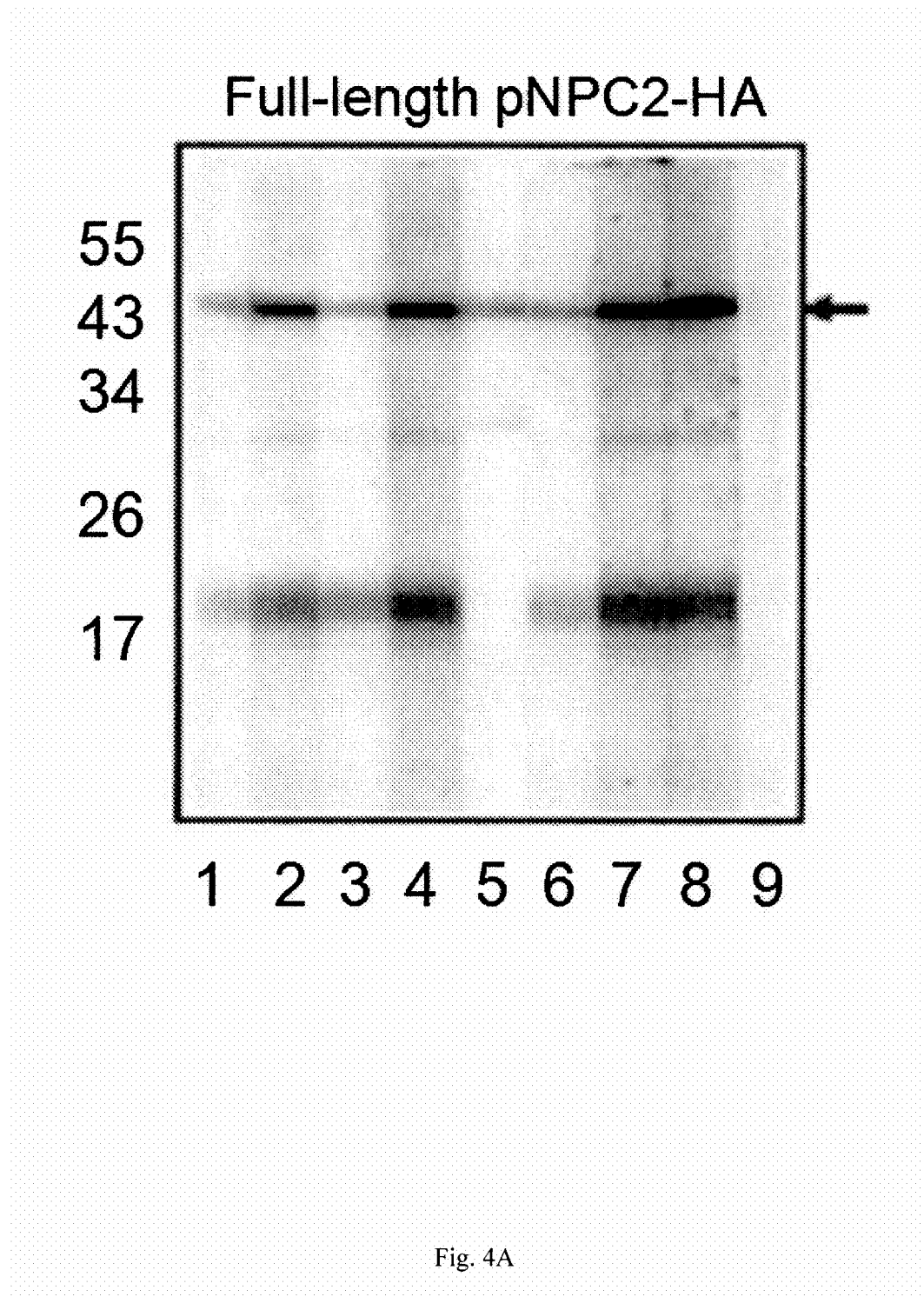
FIG. 4A illustrates epitope region mapping of anti-NPC2 monoclonal antibody (full length of pNPC2-HA).
Figure 4B:
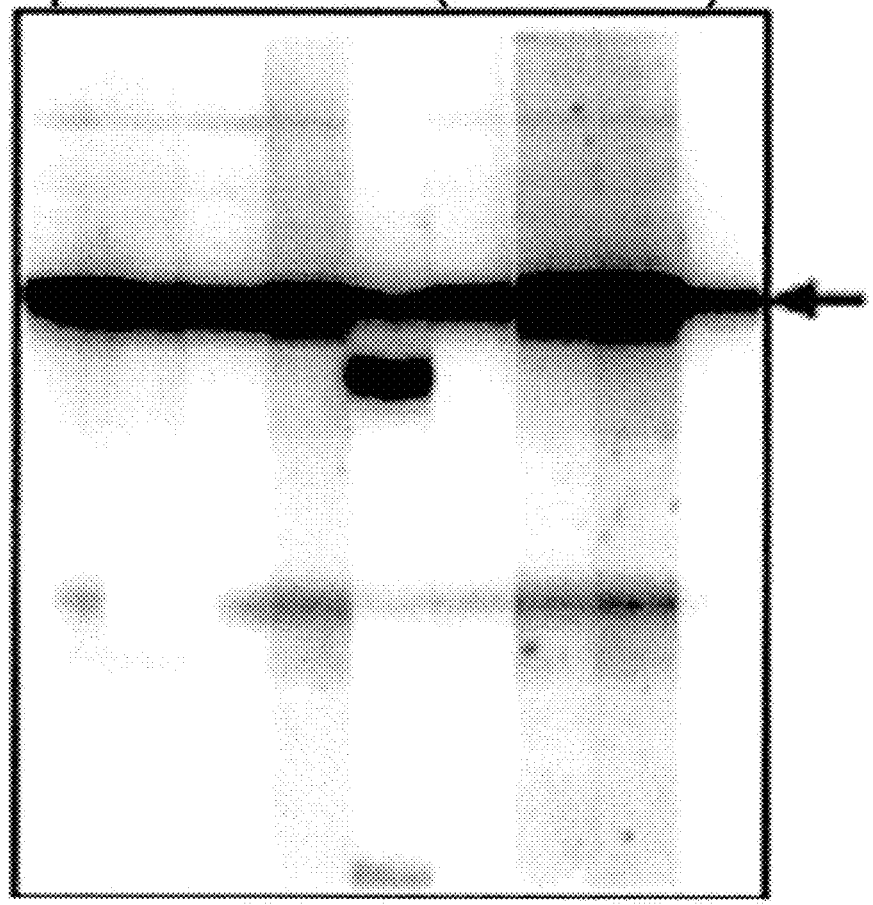
FIG. 4B illustrates epitope region mapping of anti-NPC2 monoclonal antibody (1-80 a.a).
Figure 4C:
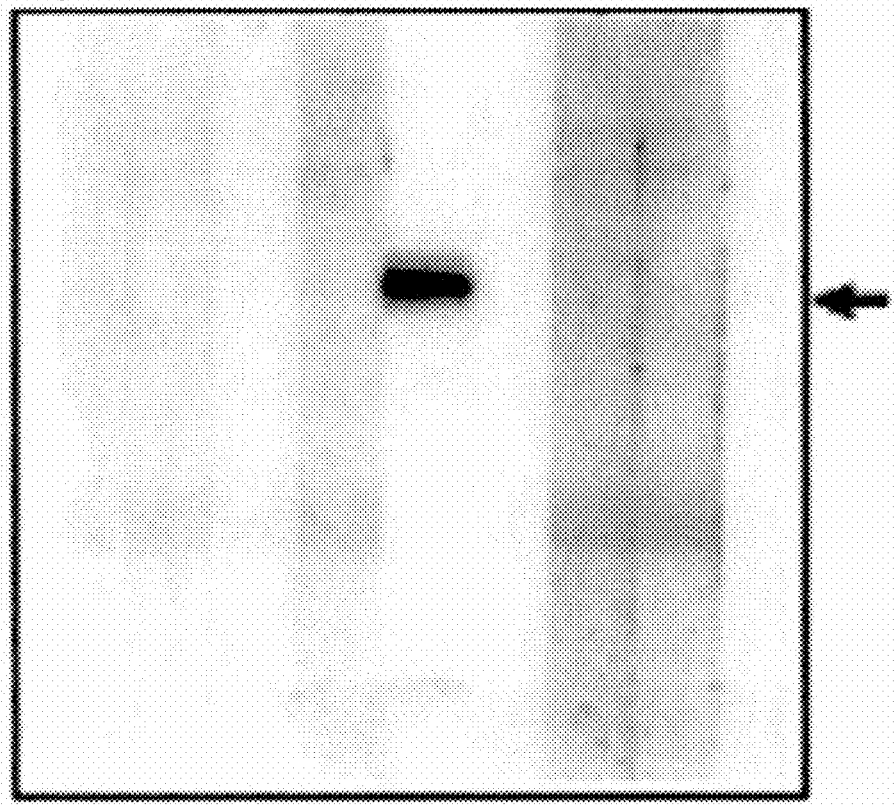
FIG. 4C illustrates epitope region mapping of anti-NPC2 monoclonal antibody (81-151 a.a).
Figure 4D:
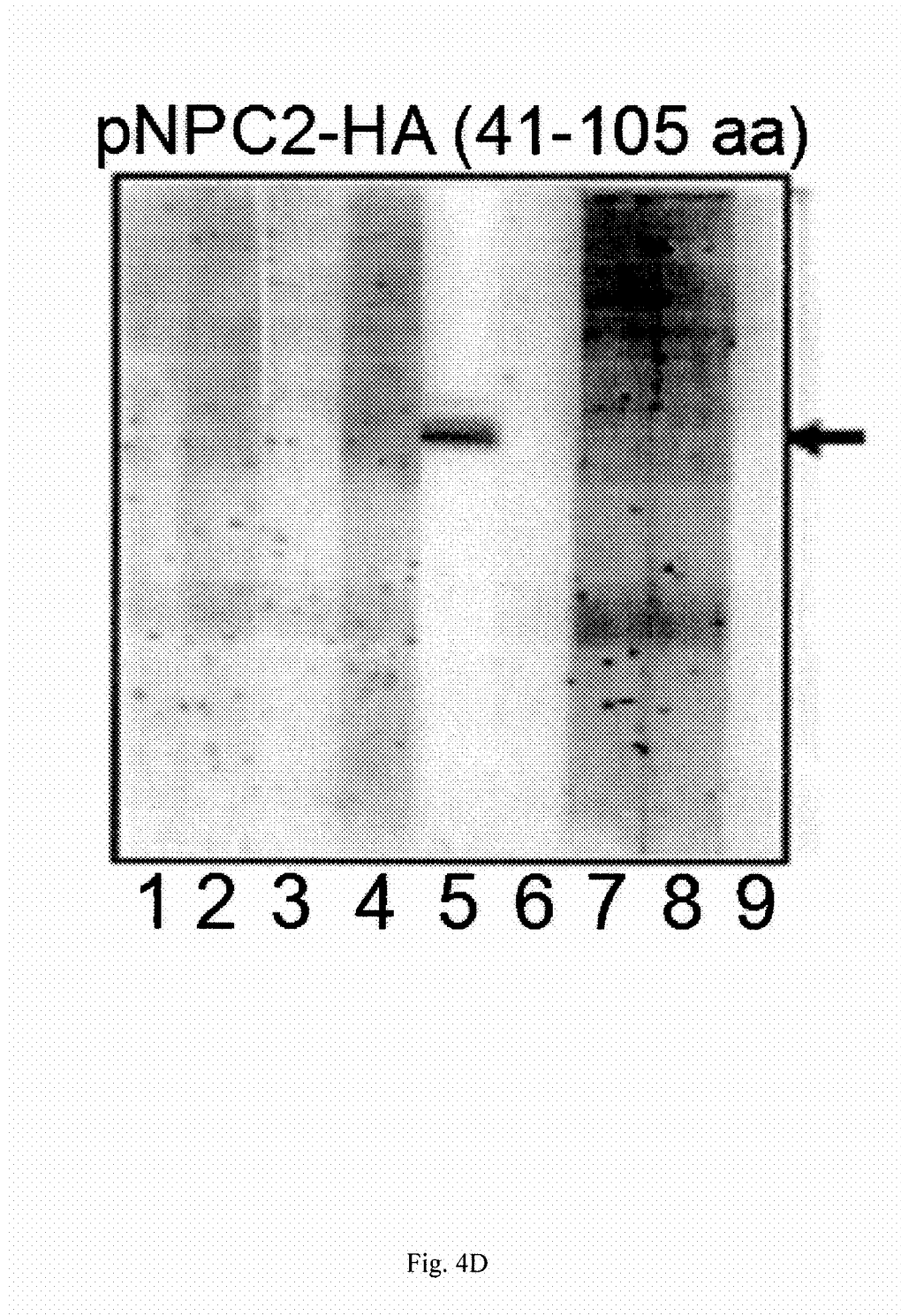
FIG. 4D illustrates epitope region mapping of anti-NPC2 monoclonal antibody (41-105a.a.).

Using mouse epididymic cells (known as expressing NPC2 protein) were used as a sample to test the reactivity of the antibodies of example 1 by western-blotting. These results are shown in FIG. 2. In addition, these mAbs can specifically recognize mouse epididyme, which is a NPC2 abundantly expressed in tissue. In FIG. 2, the results are 14-8D, 5-5B, pre-immune serum (negative control), 5-4B, 4-12C, 3-6B, positive control, 2-7B, 1-5B and 1-2G from left to right. Besides, the Mw of GST-NPC2 and His-NPC2 are at the position of 43 and 17. All of the monoclonal antibodies showed a good reactivity against His-NPC2 and GST-NPC2.

Example 3

The Epitope Region of NPC2 Monoclonal Antibody

In order to map the epitope region of monoclonal NPC2 antibodies, different lengths of pNPC2-HA including full-length pNPC2-HA, N-terminal half (1-80 amino acid), 41-105 amino acid and C-terminal half (81-151 amino acid) were transfected into 293T cells for 24 hrs and harvested for western blot analysis.

As shown in FIG. 4A-4D, the arrows indicate the epitope region, and the No. 1-9 represents the monoclonal antibodies of 14-8D. 5-5B, 5-4B, 4-12C, positive control, 3-6B, 2-7B, 1-5B and 1-2G respectively. All eight NPC2 monoclonal antibodies can recognize full length and N-terminal half (1-80 aa) of pNPC2-HA. While, 41-105 as and C-terminal half (81-151 aa) of NPC2 were not the NPC2 monoclonal antibodies binding sites.

Taken together, all of the anti-NPC2 monoclonal antibodies recognize amino acids 1-40 of NPC2 protein, MRFLAATFLLLALSTAAQAEPVQFKDCGSVDGVIKEVNVS (SEQ NO.2).

Example 4

The Epitope Region of Anti-NPC2 Monoclonal Antibody 3-6B

Peptide Screening was used to identify the epitope region of anti-NPC2 monoclonal antibody (3-6B), synthesized 4 peptides of 10 as which includes N-terminal half (1-40 aa) of NPC2. Then, the epitope region was identified by enzyme immunoassay (EIA).

The synthesized peptides were coated on an EIA 96 well plate by 10 ug/ml (in 68 mM NaHCO3 and 32 mM NaCO3, PH 9.6) and blocked by 2% BSA in PBST. Then, primary antibody 3-6B was reacted for 1 hr in 37° C. and washed by PBST (PBS+0.05% TWEEN 20) for 4 times. Next, secondary antibody anti-mouse IgG HRP (1:3000) was added and reacted for 1 hr in 37° C., and then washed by PBST (PBS+0.05% TWEEN 20) wash for 4 times. Then, OPD and 3N HCl were added to stop the reaction, and an ELx808 enzyme immunoassay analyzer was used at a wavelength of 490 nm.

Figure 5:
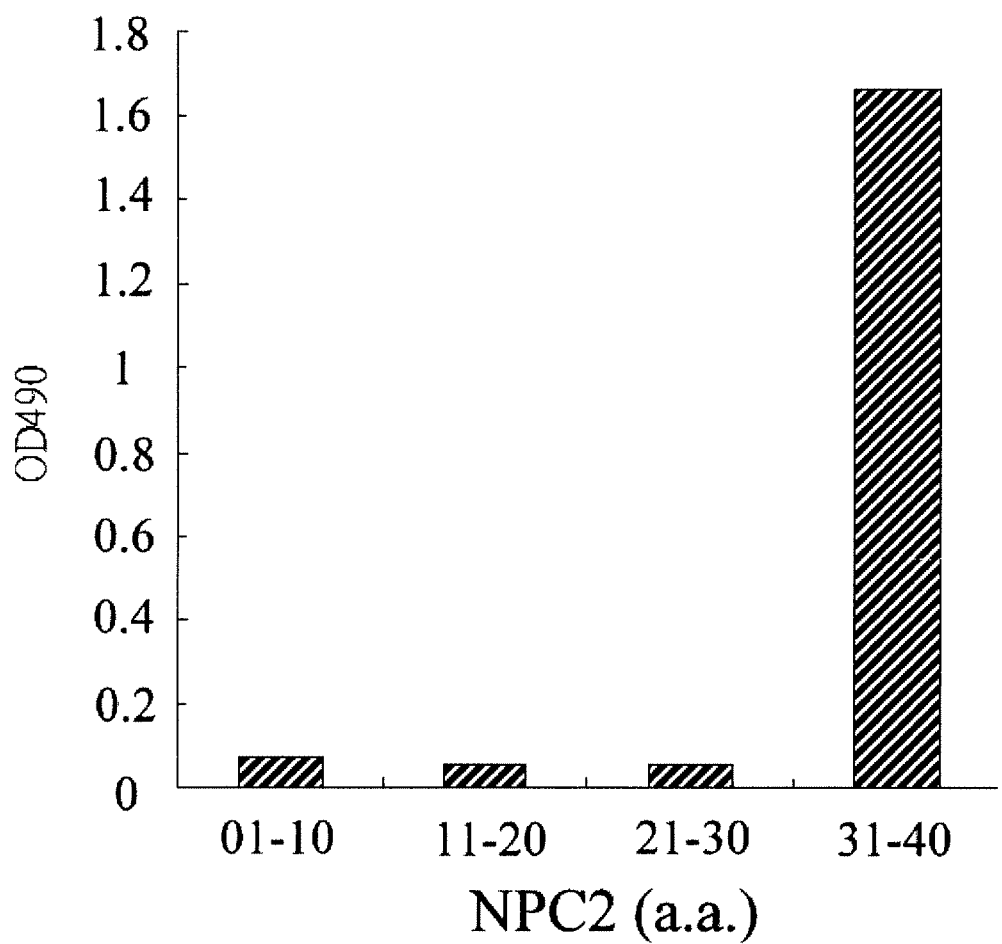
FIG. 5 shows the detecting of epitope region of monoclonal NPC2 antibody (3-6B).

The are shown in table 2, where the OD490 of peptide NPC2-3140 by anti-NPC2 monoclonal antibody (3-6B) are 1.716 and 1.607, the other peptides are lower than 0.1 (Table 2). The average of OD490 showed in FIG. 5.

Therefore, the epitope region of anti-NPC2 monoclonal antibody (3-6B) is 31~40 aa of N-terminal of NPC2 and the sequences is: DGVIKEVNVS (SEQ NO.3)

TABLE 2

Enzyme immunoassay of anti-NPC2 monoclonal antibody (3-6B)

| NPCR peptides | Optical density, OD)(average) | OD1 | OD2 |
|---|---|---|---|
| NPC2 01-10aa | 0.0775 | 0.084 | 0.071 |
| NPC2 11-20aa | 0.056 | 0.054 | 0.058 |
| NPC2 21-30aa | 0.057 | 0.054 | 0.06 |
| NPC2 31-40aa | 1.6615 | 1.716 | 1.607 |

Example 5

The Sensitivity of Anti-NPC2 Monoclonal Antibody 3-6B

The sensitivity of anti-NPC2 monoclonal antibody (3-6B) was detected from shNPC2 transfected Sk-hep1 cells, which are known as NPC2 expressing cells. ShNPC2 was transfected into Sk-hep1 cells to knock down the NPC2, and the vector was used with and without the shNPC2 gene, for analysis by western-blotting. Besides, α-tubulin was used as a control.

Figure 6:
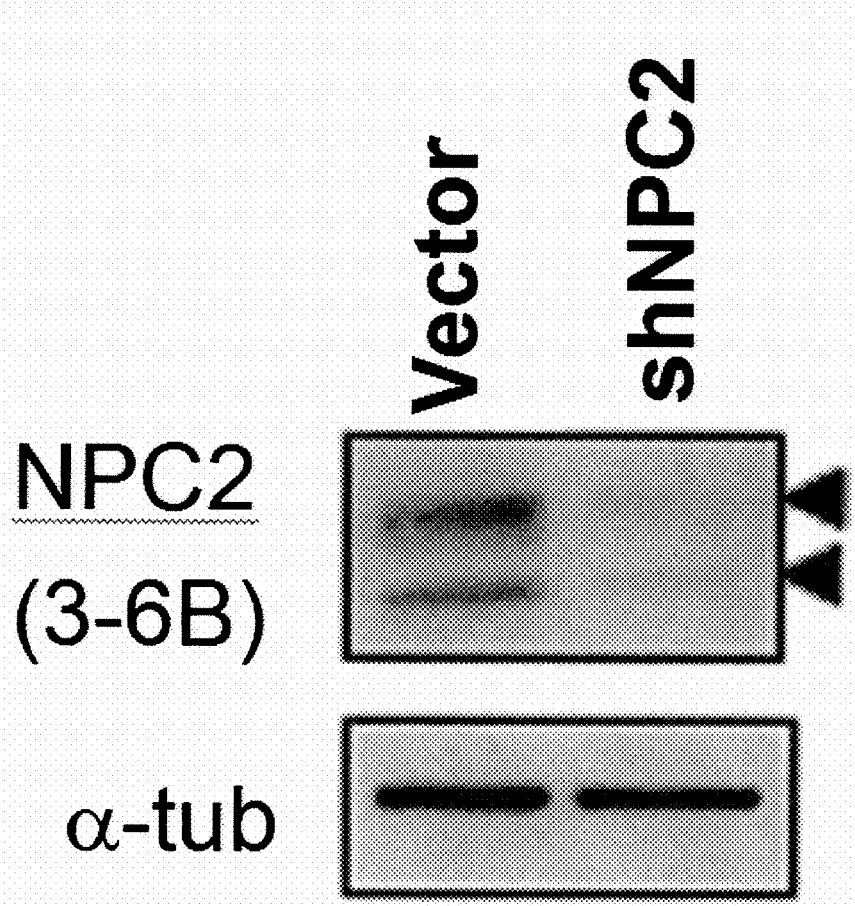
FIG. 6 shows the knockdown effect of shNPC2 in sk-hep1 cells was detected using anti-NPC2 monoclonal antibody.

As shown in FIG. 6, the anti-NPC2 monoclonal antibody can recognize the NPC2 protein in Sk-hep1 cells but can not detect it in shNPC2 transfected cells.

Therefore, the anti-NPC2 monoclonal antibody (3-6B) has a high sensitivity to NPC2.

Example 6

The Expression of NPC2 in MCD Diet Induced Fatty Liver Tissues and Serum

It has been reported that feeding mice with a methionine and choline deficient (MCD) diet results in hepatic steatosis and steatohepatitis, which mimics non-alcoholic steatohepatitis in human. Therefore, we decided to utilize such a model to investigate the roles of NPC2 in steastosis using our monoclonal NPC2 antibody.

Figure 7:
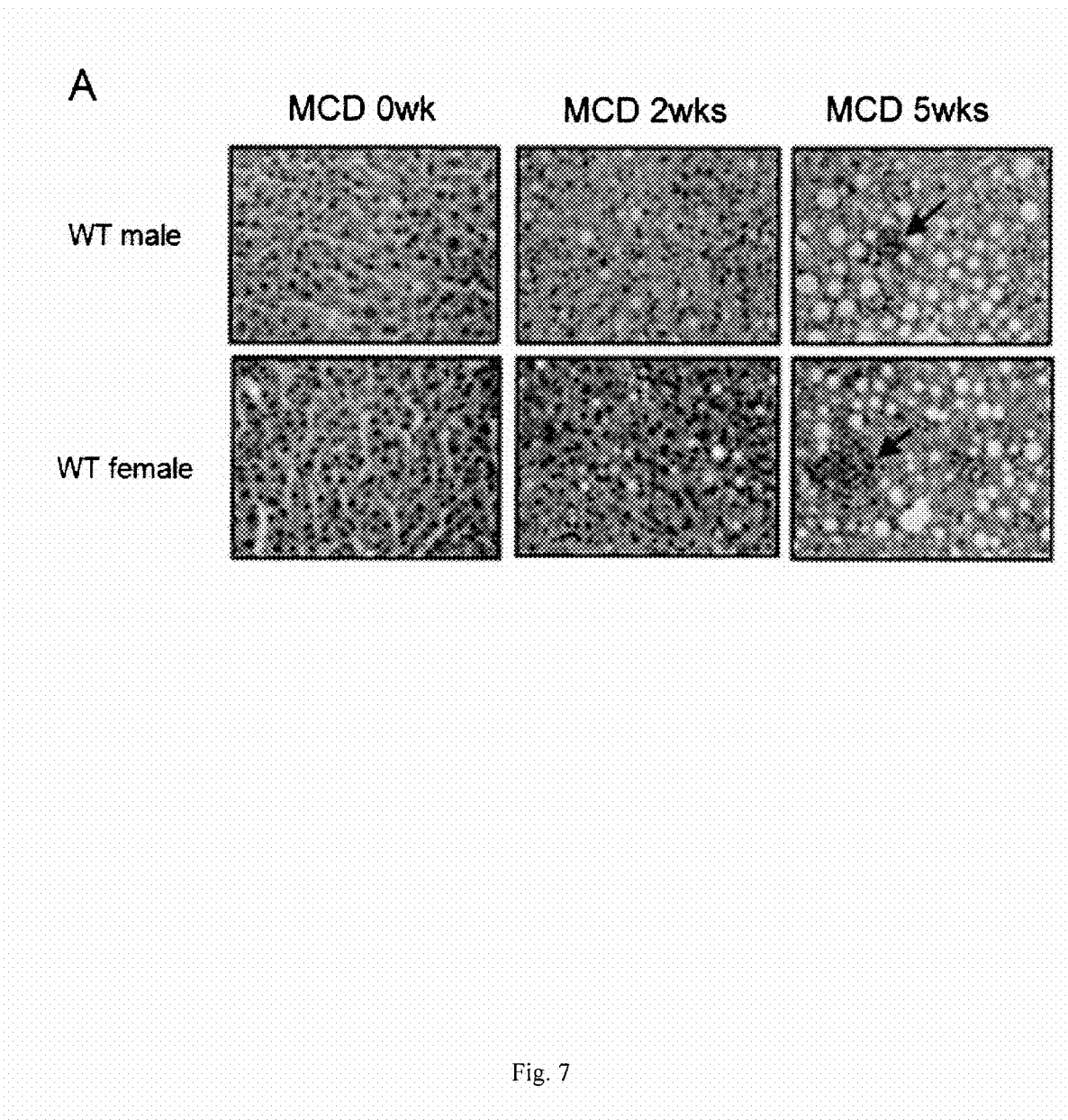
FIG. 7 shows the H&E staining of the MCD diet-induced steatohepatitis liver tissues from both genders of WT mice.

H&E staining of MCD mice liver tissue following 1, 2 and 5 weeks of MCD is demonstrated in FIG. 7.

In FIG. 7, the upper and lower rows represent the H&E staining of male mice and female mice, respectively. And from left to right are H&E staining of liver tissues from normal, 2 weeks MCD and 5 weeks MCD mice. Wherein the MCD diet begins to induce steatosis at the second week and inflammatory infiltration at the fifth week (shown as arrows).

Figure 8:
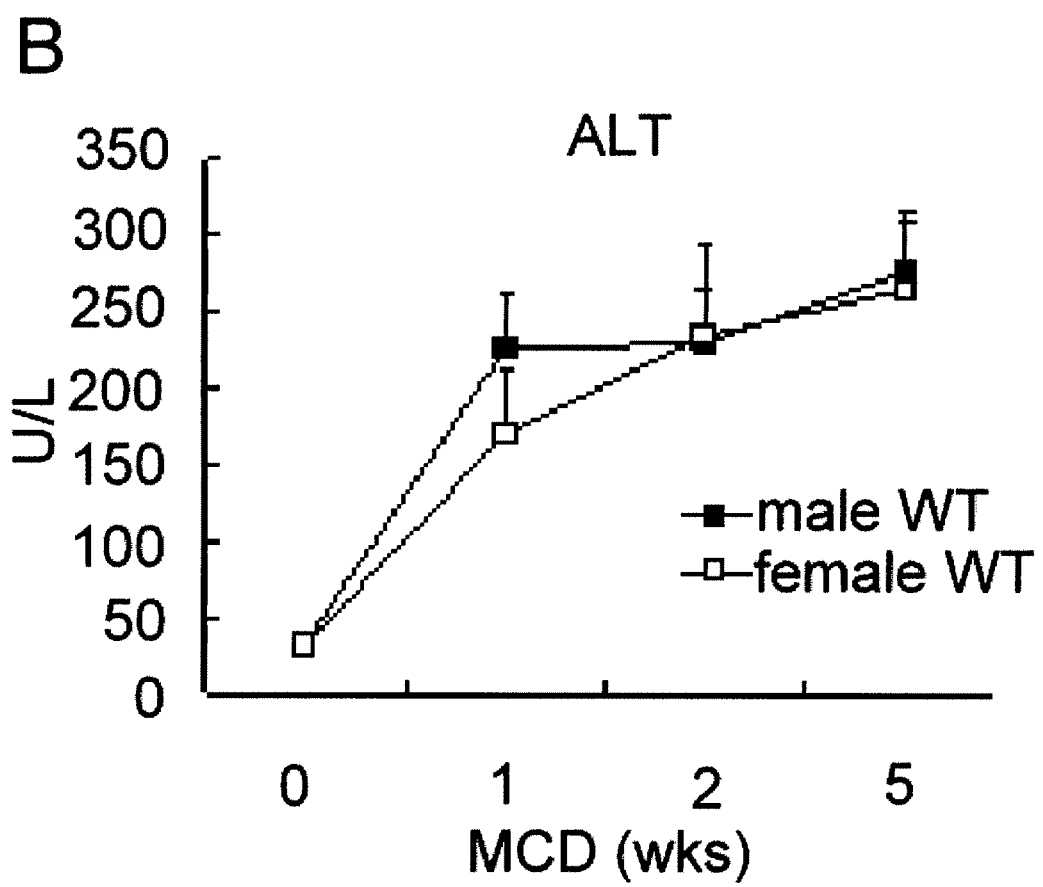
FIG. 8 shows the serum ALT levels from 0, 1, 2 and 5 weeks of MCD fed WT mice.

As expected, the MCD diet begins to induce steatosis at the second week and steatohepatitis and abnormal serum ALT levels at the fifth week (FIG. 8). In both male and female mice, as the MCD duration increases, the ALT levels gets higher. The unit of y-axis is U/L (U=unit, L=liter).

Figure 9:
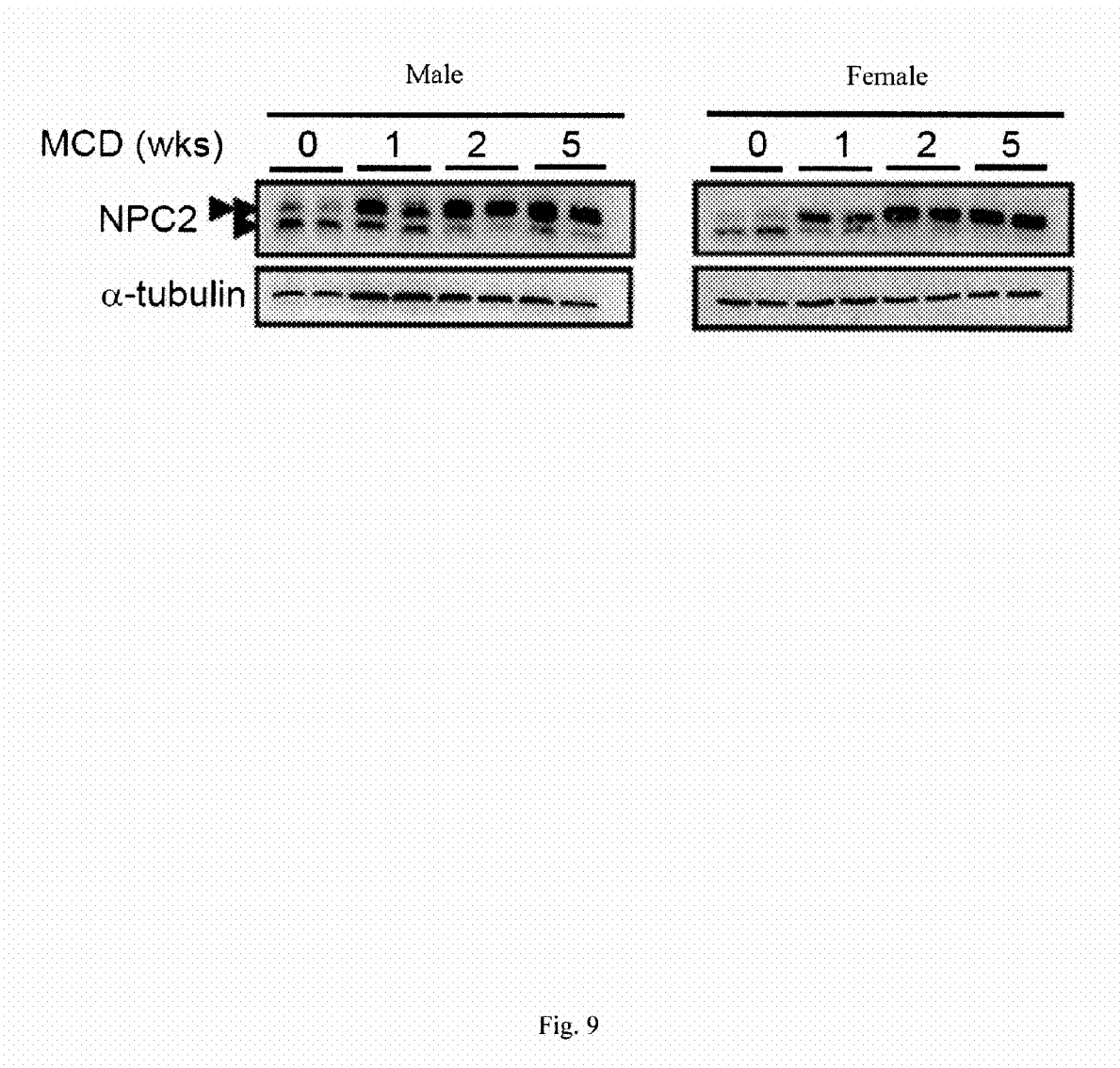
FIG. 9 shows the expression level of glycosylated-NPC2 is enhanced in MCD fed WT mice.

Next, 1:2000 diluted anti-NPC2 monoclonal antibody 3-6B was used to observe glycosylated-NPC protein level of the liver cell extract in male and female MCD mice by western blot analysis. As shown in FIG. 9, that glycosylated-NPC2 was significantly enhanced as the MCD treatment.

Figure 10:
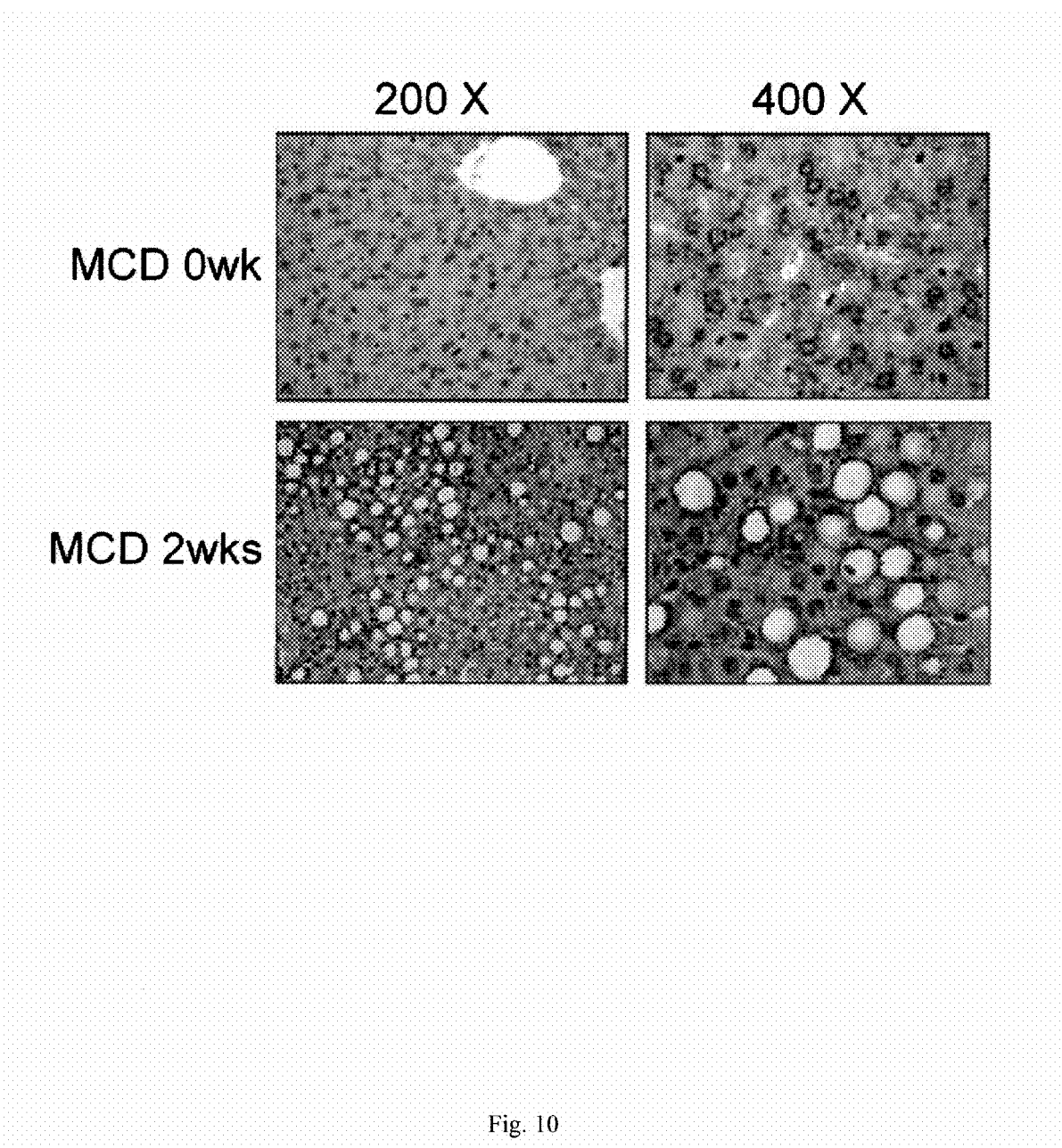
FIG. 10 shows the IHC staining of NPC2 using monoclonal NPC2 antibody (3-6B).

Besides, 1:200 diluted anti-NPC2 monoclonal antibody 3-6B was used to observe glycosylated-NPC of 5 weeks MCD mice by IHC staining. As shown in FIG. 10, IHC staining of mouse normal and fatty liver tissues showed that NPC2 displayed an enlargement of punctuate structure in steatosis region compared to the steatosis-adjacent tissues.

Figure 11:
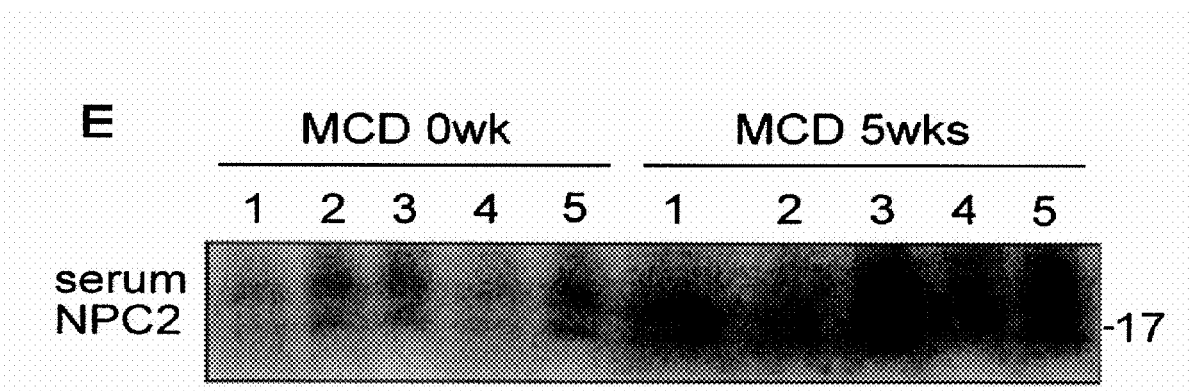
FIG. 11 shows the western blot of serum sample MCD fed WT mice using monoclonal NPC2 antibody (3-6B).

In addition, serum levels of NPC2 were enhanced followed by 5 weeks of MCD diet-induced steatohepatitis model (FIG. 11), suggesting that the increasing of NPC2 in serum may correlate to the progression of hepatosteatosis in mice.

Example 7

IHC Staining of NPC2 in Human Fatty Liver and HCC Tissues

Figure 12:
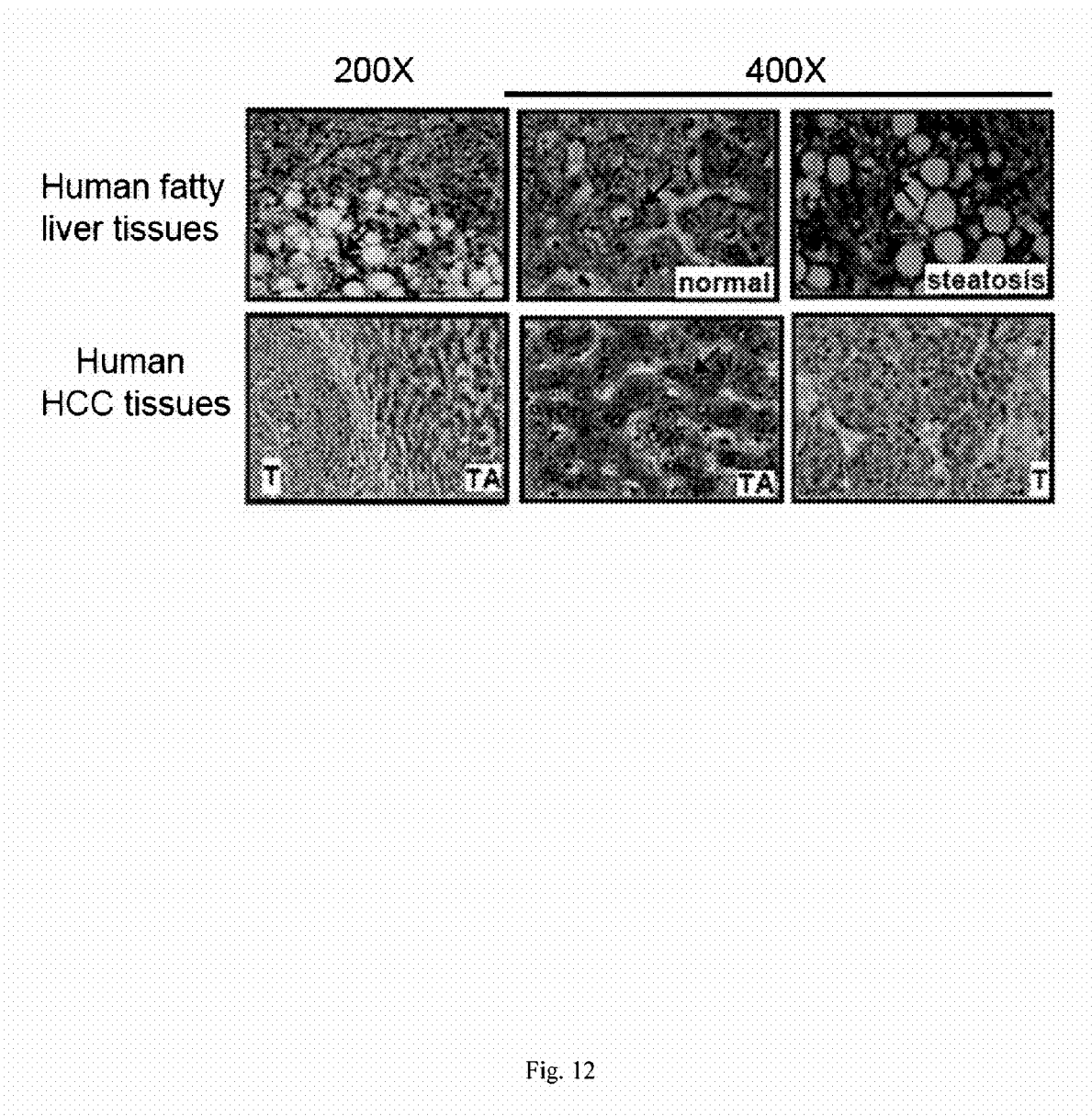
FIG. 12 shows the immunohistochemical staining of 46 pairs of human fatty liver and 50 pairs of HCC tissues using monoclonal NPC2 antibody (3-6B).
Figure 13:
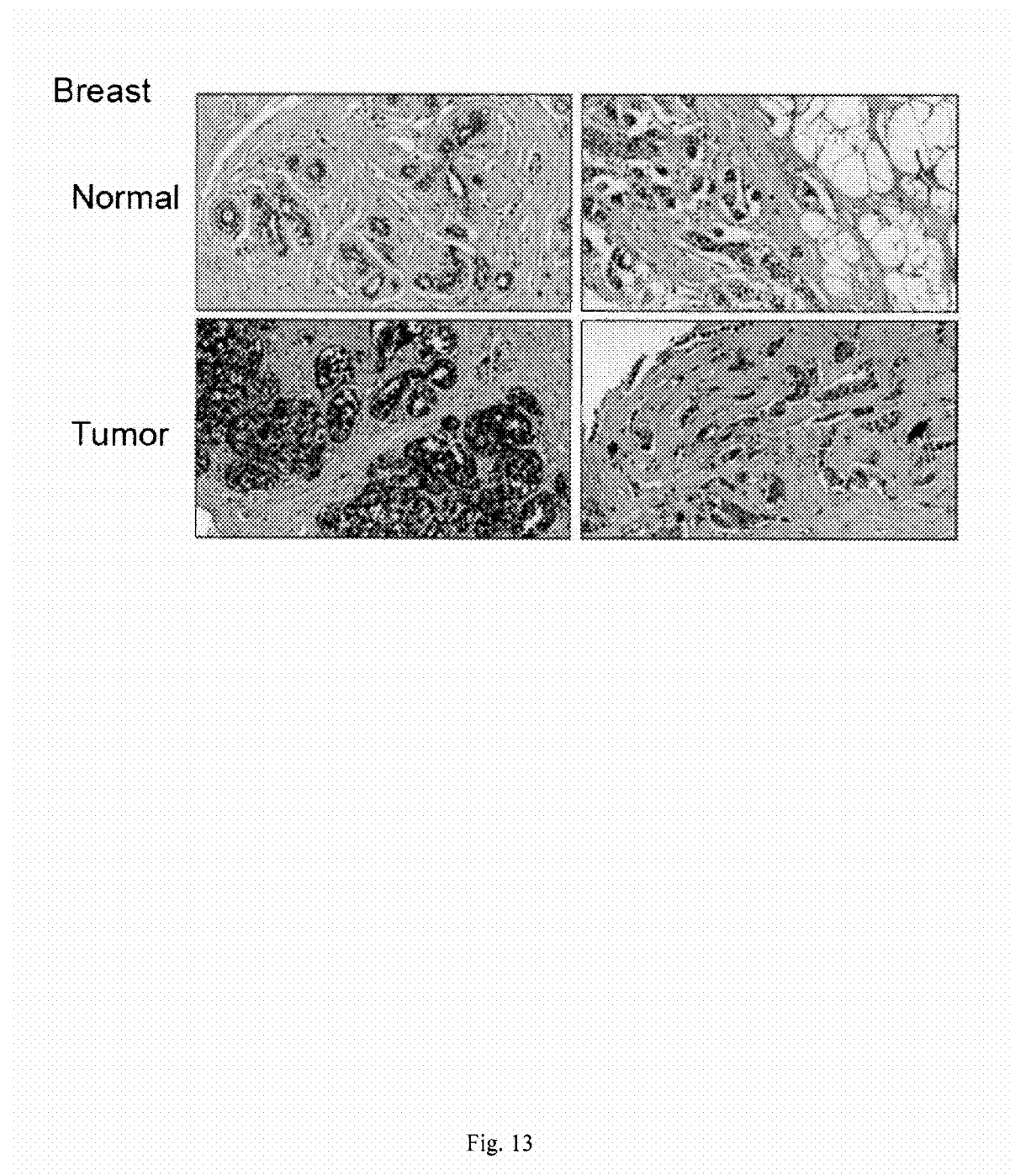
FIG. 13 shows the protein level of NPC2 in breast cancer cell.
Figure 14:
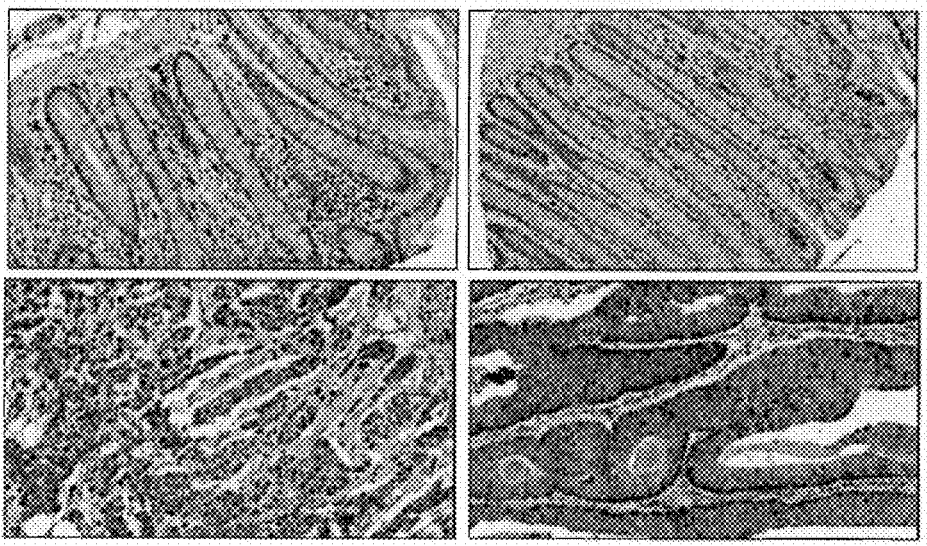
FIG. 14 shows the protein level of NPC2 in colon cancer cell.
Figure 15:
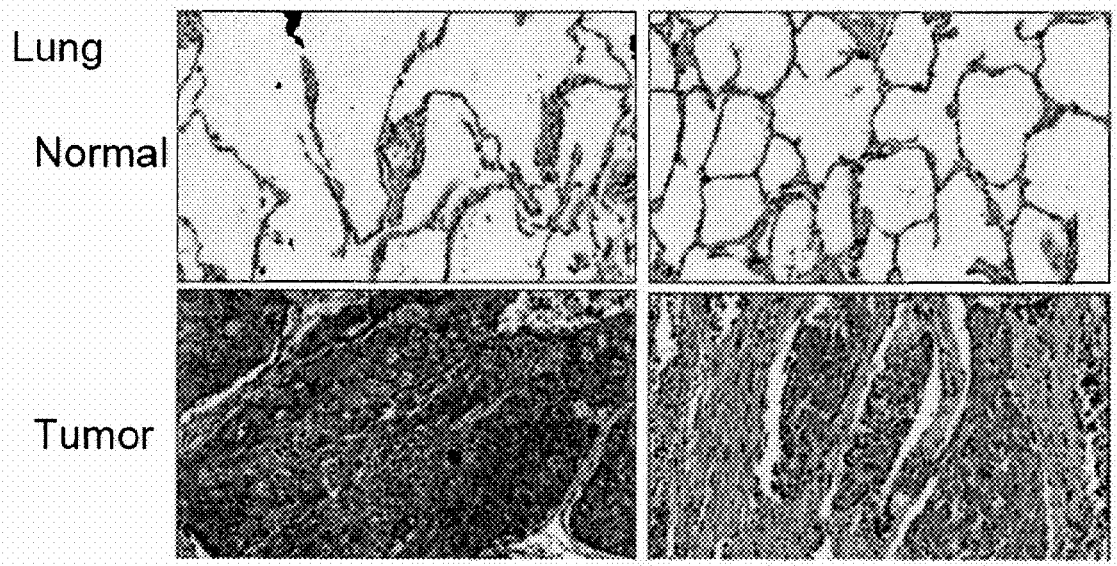
FIG. 15 shows the protein level of NPC2 in lung cancer cell.
Figure 16:
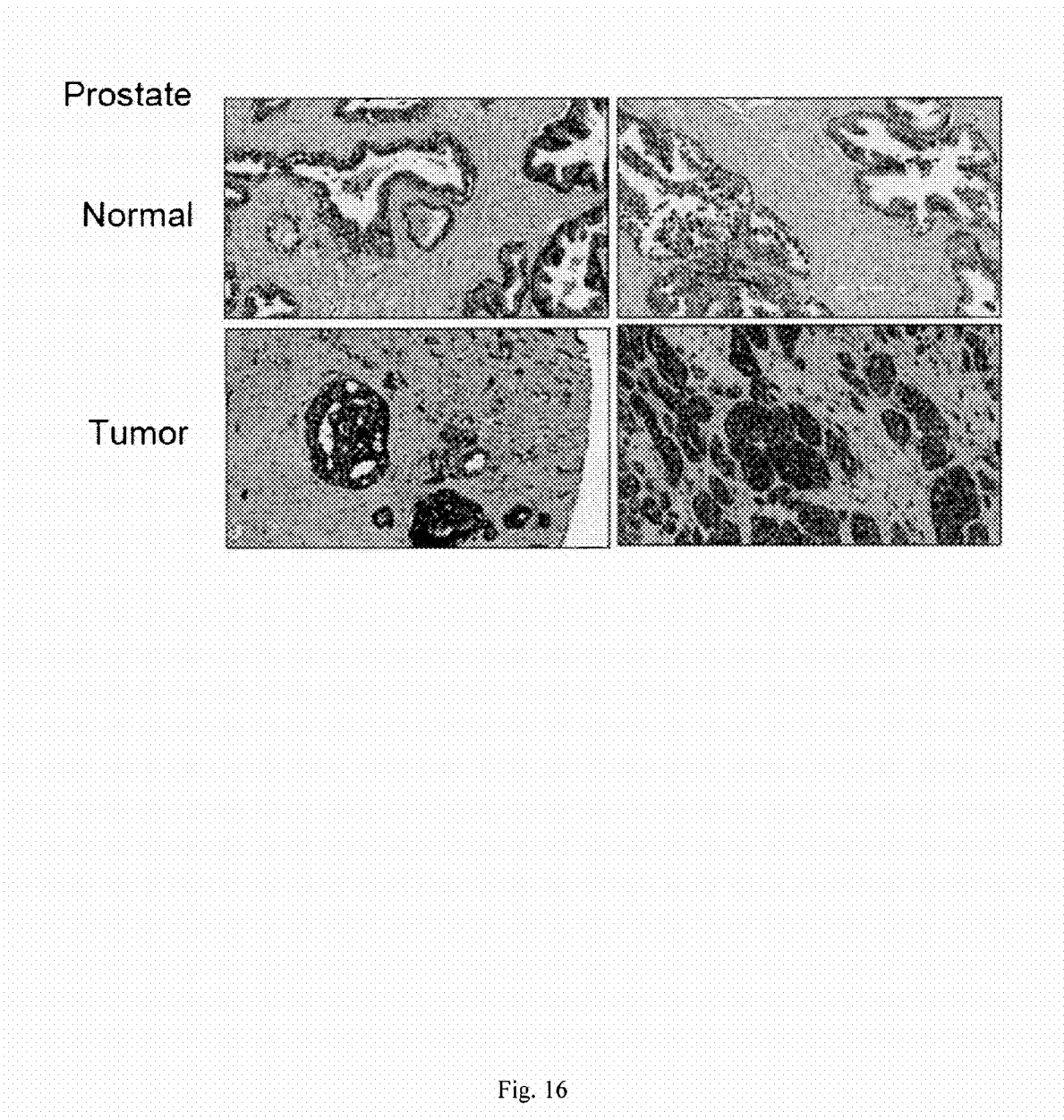
FIG. 16 shows the protein level of NPC2 in prostate cancer cell.
Figure 17:
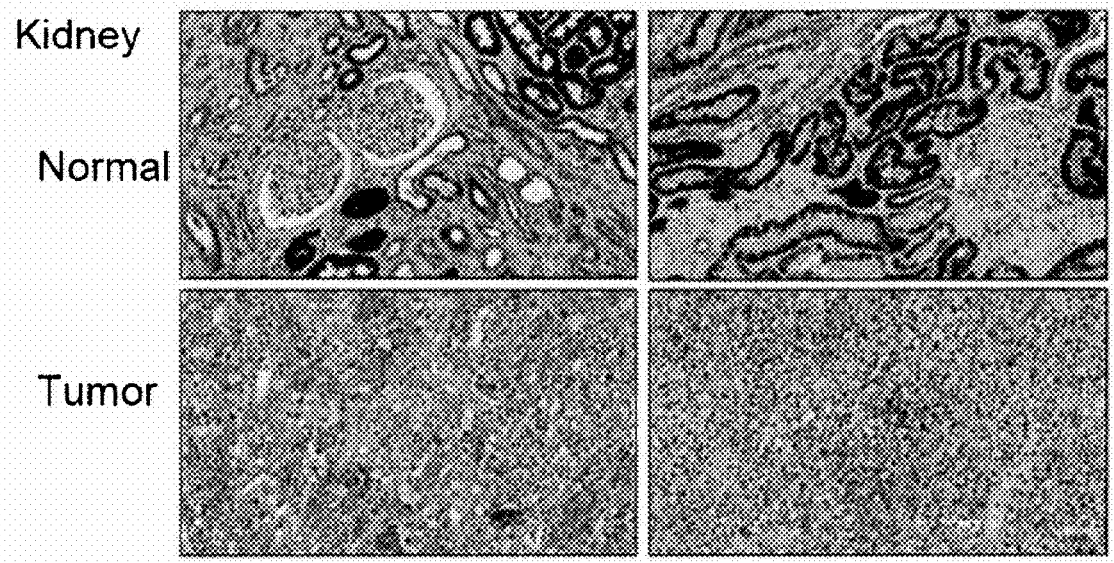
FIG. 17 shows the protein level of NPC2 in kidney cancer cell.
Figure 18:
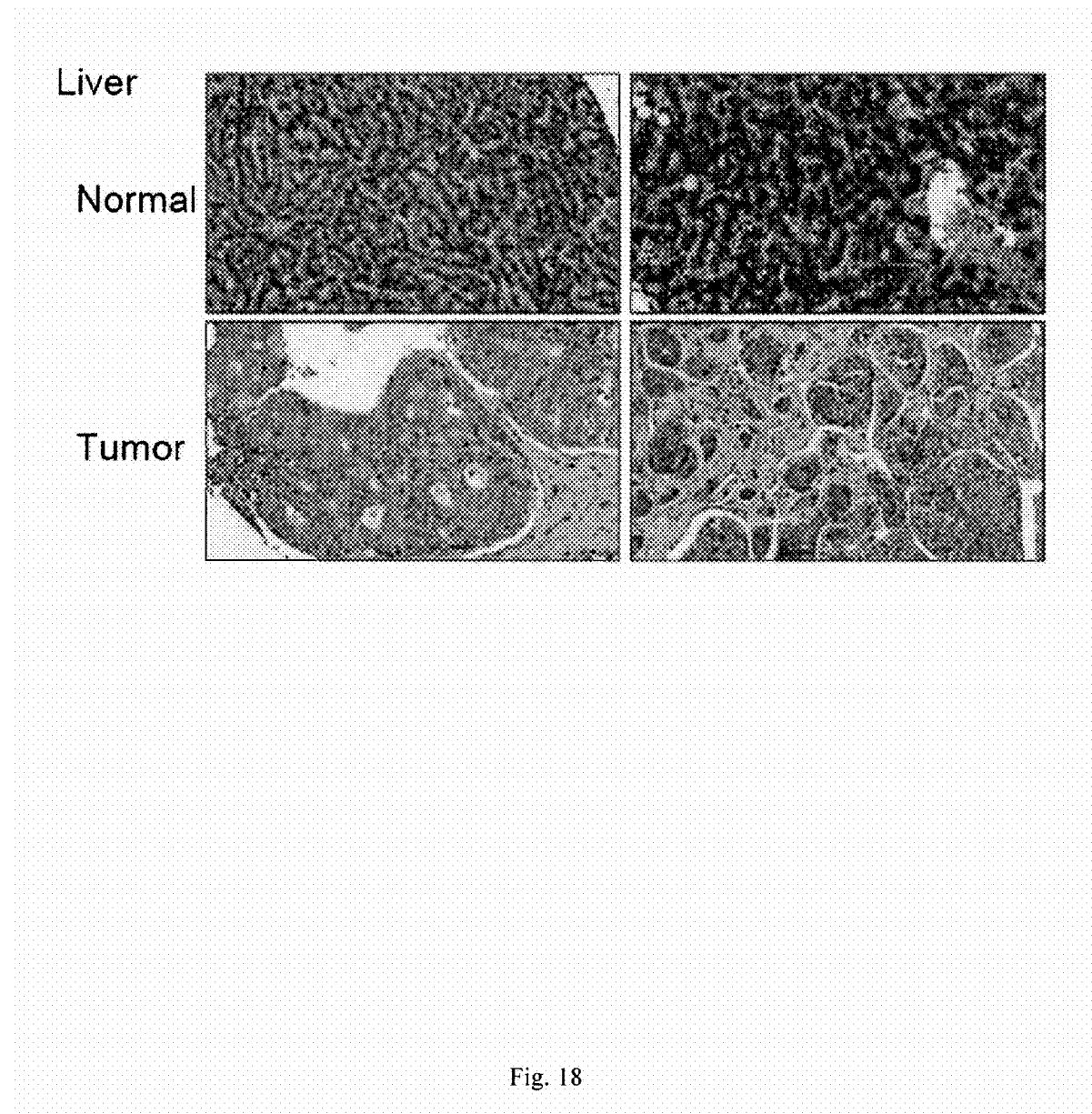
FIG. 18 shows the protein level of NPC2 in hepatic cancer cell.

The expression of NPC2 in human fatty liver and HCC tissues was evaluated using immunohistochemical (IHC) staining. The results showed that among 56 pairs of steatosis (S) and steatosis adjacent (SA) tissues, 41 (73%) steatosis tissues had higher NPC2 expression, 10 (18%) had equal level and 5 (9%) had lower expression than their SA tissue counterparts (FIG. 12, upper panel). The difference of the NPC2 expression between steatosis and steatosis adjacent tissues is statistically significant (Wilcoxon Signed Ranks Test, p=0.02).

We further analyzed the expression levels of NPC2 in 50 pairs of tumor (T) and tumor-adjacent (TA) tissues from HCC patients using IHC staining. Importantly, 72% (36/50) tumor tissues had significant lower expression level of NPC2 than the tumor-adjacent tissues (FIG. 12, lower panel).

The statistic result shows in Table 3:

TABLE 3

IHC staining of NPC2 in human fatty liver and HCC tissues

Human fatty liver tissues

| S < SA N (%) | S = SA N (%) | S > SA N (%) | p value |
|---|---|---|---|
| 5 (9%) | 10 (18%) | 41 (73%) | 0.02* |

Human HCC tissues

| T < TA N (%) | T = TA N (%) | T > TA N (%) | p value |
|---|---|---|---|
| 36 (72%) | 12 (24%) | 2 (4%) | 0.02* |

S = steatosis tissue; SA = steatosis-adjacent tissue; T = tumor tissue; TA = tumor-adjacent tissue.

Taken together, the data implies that the changes of NPC2 expression may reflect the pathogenesis of steatosis and subsequent HCC development. It is important to note that the most common form of chronic liver disease is non-alcoholic fatty liver disease, which encompasses a clinicopathologic spectrum of disease ranging from isolated hepatic steatosis to NASH, which can progress to cirrhosis HCC. Until now, the alteration of NPC2 expression pattern in fatty liver and HCC has not been observed in any publications. Besides, the level of NPC2 in serum can reflect to the process of steatohepatitis. Therefore, our data indicated that the applications of our NPC2 monoclonal antibody are helpful for the clinical diagnosis and research of non-alcoholic fatty liver disease.

Example 8

The Expression of NPC2 in Multiple Cancer Tissues

In order to investigate the clinical application of NPC2 monoclonal antibodies, we detected the expression of NPC2 in various normal and cancer tissues using IHC staining. FIG. 13~18 shows the IHC staining of cancer tissues in 23 breast cancer patients, 38 colon cancer patients, 44 lung cancer patients, 60 prostate cancer patients, 33 kidney cancer patients and 50 liver cancer patients respectively and the statistic results are shown in Table 4-9.

Comparing these normal tissues and their corresponding tumor tissues, NPC2 was significantly up-regulated in breast, colon, lung, and prostate cancers. In contrast, NPC2 was significantly down-regulated in kidney and liver. While, there were no difference between normal and cancer tissues of rectum, pancreas, esophagus, stomach, ovary and uterine cervix. Taken together, these results indicated that the aberrant expression of NPC2 is associated with different cancers.

TABLE 4

The NPC protein level in breast cancer patients and in normal people.

| n = 23 | T > N | T = N | T < N | P value |
|---|---|---|---|---|
| n (%) | 18 (78%) | 4 (17%) | 1 (4%) | <0.01 |

TABLE 5

The NPC protein level in colon cancer patients and in normal people.

| n = 38 | T > N | T = N | T < N | P value |
|---|---|---|---|---|
| n (%) | 18 (47%) | 14 (37%) | 6 (16%) | 0.045 |

TABLE 6

The NPC protein level in lung cancer patients and in normal people.

| n = 44 | T > N | T = N | T < N | P value |
|---|---|---|---|---|
| n (%) | 36 (82%) | 5 (11%) | 9 (20%) | <0.01 |

TABLE 7

The NPC protein level in prostate cancer patients and in normal people.

| grade | T (n = 60) | | | | | N (n = 9) | | | | P value |
|---|---|---|---|---|---|---|---|---|---|---|
| | − | ± | 1+ | 2+ | 3+ | − | ± | 1+ | 2+ | |
| n (%) | 1 (5%) | 3 (5%) | 22 (37%) | 25 (42%) | 9 (15%) | 1 (11%) | 0 | 6 (66%) | 2 (22%) | 0.05 |

TABLE 8

The NPC protein level in kidney cancer patients and in normal people.

| n = 33 | T > N | T = N | T < N | P value |
|---|---|---|---|---|
| n (%) | 2 (6%) | 0 | 31 (94%) | <0.001 |

TABLE 9

The NPC protein level in liver cancer patients and in normal people.

| n = 50 | T > N | T = N | T < N | P value |
|---|---|---|---|---|
| n (%) | 2 (4%) | 12 (24%) | 36 (72%) | 0.02 |

As mentioned above, NPC2 protein level can be an index of cancer development. Therefore, the present invention of anti-NPC2 monoclonal antibody can be used for cancer detection.

What is claimed is:

1. An isolated and biologically pure NPC2 (Niemann-Pick C2) monoclonal antibody for detecting fatty liver, wherein:
   the monoclonal antibody specifically binds an N-terminal epitope contained in the amino acid sequence of NPC2 protein consisting of SEQ ID NO: 3;
   the monoclonal antibody can specifically bind to the NPC2 protein whether the NPC2 protein is glycosylated or not;
   the monoclonal antibody comprises an IgG2a heavy chain and kappic light chain; and
   the OD490 value of the monoclonal antibody binding to the N-terminal epitope is about 1.6 to 1.7.

2. A method of detecting fatty liver tissue in an organism, which includes the steps of:
   (a) providing test tissue from a mammal suspected of having fatty liver tissue and providing normal liver tissue;
   (b) contacting the test tissue and the normal tissue with the antibody of claim 1 during performance of a detecting method and thereby detecting an expression level of NPC2 protein or glycosylated NPC2 protein in the test tissue and the normal tissue; and
   (c) determining the expression level, wherein when the expression level of NPC2 protein or glycosylated NPC2 protein in the test tissue is about 2 fold higher than the expression level of the normal tissue this means the tested organism suffers from fatty liver.

3. The method of claim 2, wherein the detecting method is selected from the group consisting of western-blotting, immunoprecipitation and immunohistochemistry.

4. A method of detecting liver cancer or kidney cancer in an organism, which includes the steps of:
   (a) providing test tissue from a mammal suspected of having liver cancer or kidney cancer, and providing normal tissue, wherein the test tissue is from an area of the mammal where the cancer is suspected;
   (b) contacting the test tissue and the normal tissue with the antibody of claim 1 during performance of a detecting method and thereby detecting an expression level of NPC2 protein or glycosylated-NPC2 protein in the test tissue and the normal tissue; and
   (c) determining the expression level, wherein when the expression level of NPC2 protein or glycosylated-NPC2 protein in the test tissue is about 2 fold lower than the expression level in the normal tissue this means the tested mammal has a 72% to 92% chance of suffering from liver cancer or kidney cancer.

5. The method of claim 4, wherein the detecting method is selected from the group consisting of western-blotting, immunoprecipitation and immunohistochemistry.

6. A method of detecting cancer in an organism, which includes the steps of:
   (a) providing test tissue from a mammal suspected of having cancer and providing normal tissue, wherein the test tissue is from an area of the mammal where the cancer is suspected;
   (b) contacting the test tissue and the normal tissue with the antibody of claim 1 during performance of a detecting method and thereby detecting an expression level of NPC2 protein or glycosylated-NPC2 protein in the test tissue and the normal tissue; and
   (c) determining the expression level, wherein when the expression level of the test tissue is higher than the expression level of the normal tissue, this means the tested mammal has a 47% to 83% chance of suffering from a cancer selected from the group consisting of breast cancer, colon cancer, lung cancer, and prostate cancer.

7. The method of claim 6, wherein the cancer is selected from the group consisting of hepatic cancer and kidney cancer.

8. The method of claim 6, wherein the detecting method is selected from the group consisting of western-blotting, immunoprecipitation and immunohistochemistry.

9. The method of claim 2, wherein the test tissue and the normal tissue are selected from the group consisting of blood tissue, liver tissue, or a combination thereof.

10. The method of claim 9, wherein the test tissue and the normal tissue comprise liver cells.

* * * * *